United States Patent [19]

Nehme

[11] 4,153,058
[45] May 8, 1979

[54] PLEURAL DECOMPRESSION CATHETER

[76] Inventor: Alexander E. Nehme, 6335 Brewer Rd., Flint, Mich. 48507

[21] Appl. No.: 812,608

[22] Filed: Jul. 5, 1977

[51] Int. Cl.² .................... A61M 27/00; A61B 17/34
[52] U.S. Cl. ................................ 128/347; 128/350 V
[58] Field of Search ........................... 128/347–351, 128/274, 214.4, 221

[56] References Cited

U.S. PATENT DOCUMENTS

| 733,152 | 7/1903 | Chisholm | 128/350 V |
|---|---|---|---|
| 1,509,059 | 9/1924 | Dodge | 128/274 UX |
| 2,001,638 | 5/1935 | Tornsjo | 128/347 |
| 2,867,213 | 1/1959 | Thomas | 128/350 V |
| 3,459,189 | 8/1969 | Alley et al. | 128/347 |
| 3,463,159 | 8/1969 | Heimlich | 128/350 V |

FOREIGN PATENT DOCUMENTS 36318 8/1926 Denmark .................... 128/347

Primary Examiner—Dalton L. Truluck
Attorney, Agent, or Firm—Gifford, Chandler, VanOphem, Sheridan & Sprinkle

[57] ABSTRACT

A pleural decompression catheter is provided for releasing entrapped air within a human body. The device comprises an elongated member axially insertable into a human body and having fluid passage means for establishing fluid communication from the exterior of the elongated member to one end of the member positioned exteriorly of the body. A one-way valve is coupled to the exteriorly extending end of the elongated member so that entrapped air within the body can flow through the passage means in the elongated member, through the one-way valve and exhaust exteriorly of the human body.

7 Claims, 4 Drawing Figures

U.S. Patent    May 8, 1979    4,153,058
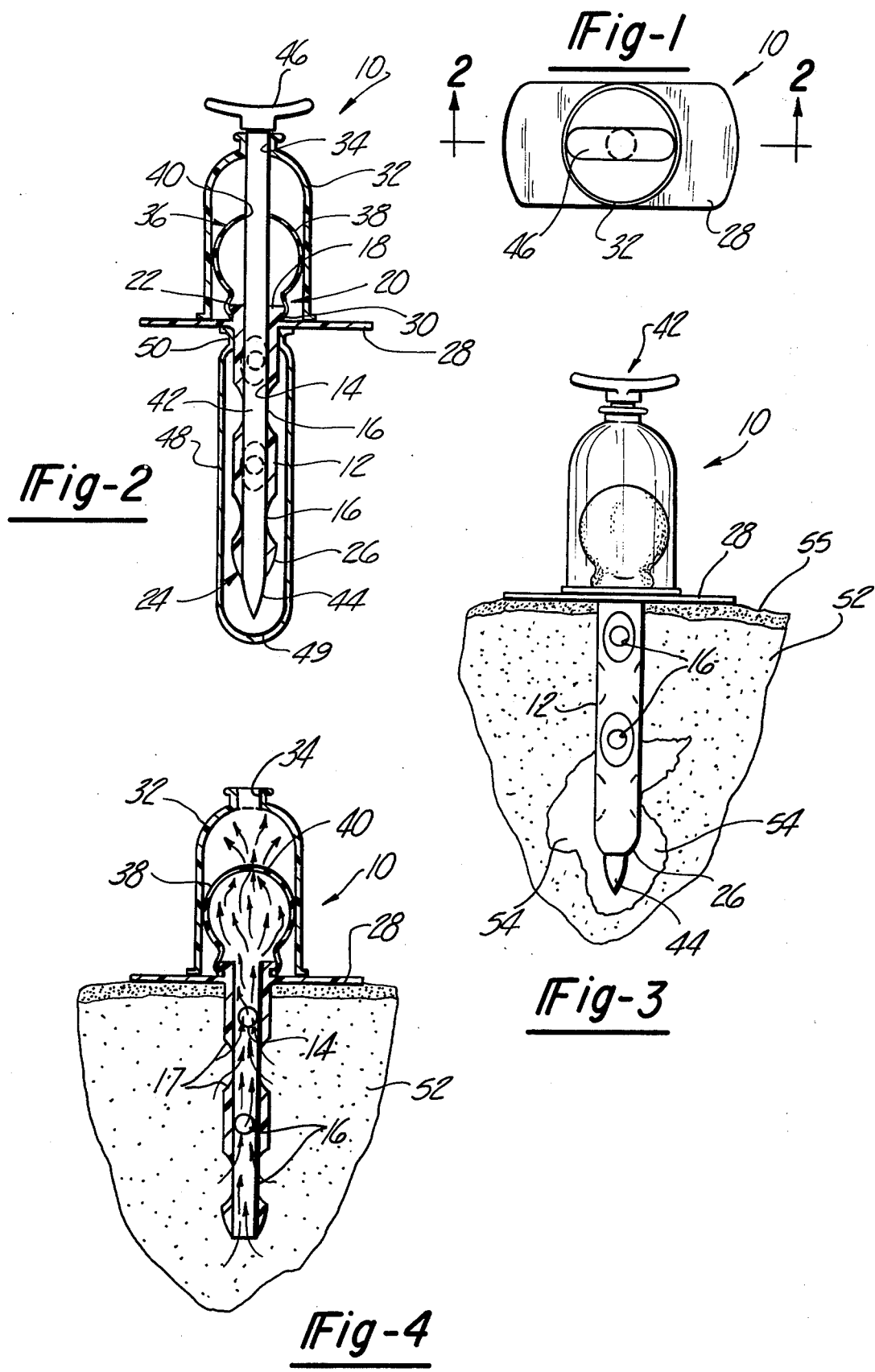

PLEURAL DECOMPRESSION CATHETER

BACKGROUND OF THE INVENTION

I. Field of the Invention

The present invention relates to a surgical device for releasing entrapped air within a human body.

II. Description of the Prior Art

Entrapped air within the human body, for example within the pleura cavity, is a relatively common event and can result from a puncture wound, collapsed lung or even following major surgery. Entrapped air within the human body is a serious health hazard and may even cause death to the person if the entrapped air enters into the bloodstream or causes a tension pneumothorax.

Previously, medical doctors have drilled relatively large holes and inserted large tubes into the body in order to release entrapped air pockets within the human body. This previously known method, however, is disadvantageous in that relatively large body tissue damage results. Moreover, this previous method may also introduce contaminates into the human body due primarily to the large drilled holes in the body.

SUMMARY OF THE PRESENT INVENTION

The present invention overcomes these above-mentioned disadvantages by providing a simple and yet effective pleural decompression catheter for releasing entrapped air within a human body.

In brief, the surgical device of the present invention comprises an elongated member adapted to be inserted into a human body so that one end of the elongated member extends outwardly from the body. A plurality of external fluid ports communicate with an axial passage formed through the elongated member to thereby establish fluid communication from the interior of the body to the outermost end of the elongated member.

In order to aid in the insertion of the elongated member into the human body, a trocar is axially insertable through the elongated member so that the trocar extends outwardly from the other end of the member. After the insertion of both the trocar and the elongated member within the human body, the trocar is removed from the elongated member thus opening the axial passageway in the elongated member.

A one-way valve is provided at the outermost end of the elongated member and only permits fluid flow from the elongated member, through the one-way valve and exteriorly of the human body. The one-way valve is preferably a flutter-type one-way valve.

In operation, the elongated member with the trocar is inserted into the human body to the entrapped air pocket and thereafter the trocar is removed. Upon removal, the fluid passageway through the elongated member is open which permits entrapped air within the human body to escape through the elongated member and one-way valve and exhaust exteriorly of the body. Once the entrapped air is released, the surgical device of the present invention is simply withdrawn from the human body.

BRIEF DESCRIPTION OF THE DRAWINGS

A better understanding of the present invention will be had upon reference to the following detailed description when read in conjunction with the accompanying drawings, wherein like reference characters refer to like parts throughout and in which:

FIG. 1 is a top plan view illustrating the surgical device of the present invention;

FIG. 2 is a sectional side view illustrating the surgical device of the present invention and taken substantially along line 2—2 in FIG. 1;

FIG. 3 is a side plan view illustrating the surgical device of the present invention inserted into a human body; and FIG. 4 is a sectional view of the surgical device of the present invention inserted into a human body and with parts removed to depict its operation.

DETAILED DESCRIPTION OF THE PRESENT INVENTION

With reference first to FIGS. 1 and 2, a surgical device 10 according to the present invention is thereshown and comprises an elongated tubular member 12 having an axial throughbore 14 and a plurality of axially and circumferentially spaced radial ports 16 having sloped sides 17 (FIG. 4) wherein each port 16 is open to the throughbore 14. An enlarged diameter portion 18 at a first end 20 of the tubular member 12 forms an outwardly extending annular flange 22 for a reason which will shortly become hereinafter apparent. The other end 24 of the elongated member 12 is tapered inwardly at 26 for a reason which will also hereinafter become apparent.

An outwardly extending flange or stop member 28 is secured to the tubular member 12 adjacent its upper end 20 but spaced slightly downwardly from the annular flange 22 thereby forming an annular groove 30 between the stop member 28 and the flange 22. A bell-shaped housing 32 is also secured to the upper side of the stop member 28 so that the housing 32 encloses the upper end 20 of the tubular member 12. The bell-shaped housing 32 also includes an upper opening 34 of substantially the same size and in registry with the throughbore 14 in the tubular member 12.

A one-way valve 36 encompasses the upper end 18 of the tubular member 12 and is contained within the bell-shaped housing 32. The one-way valve 36 is preferably a flutter-type valve and comprises a balloon 38 made of soft rubber. The lower end of the balloon 38 is resiliently received within the annular groove 30 which secures the balloon 38 to the tubular member 12. A slit 40 in the upper end of the balloon 38 permits fluid flow from the tubular member 12, through the balloon 38 and slit 40 and into the interior of the bell-shaped housing 32.

A trocar 42, preferably made of metal and having a lower pointed end 44, is insertable through the opening 34 in the bell-shaped housing 32, the balloon slit 40 and the tubular member throughbore 14, respectively, so that the pointed end 44 of the trocar 42 extends outwardly from the lower end 24 of the tubular member 12. In addition, a handle 46, constructed, for example, of plastic, is secured to the upper end of the trocar 42 to aid in the manipulation of the trocar 42.

As shown in FIG. 2, an elongated tubular guard 48 having a closed bottom 49 encloses the tubular member 12 and is retained thereto by a resilient upper lip 50. The guard 48 prevents contamination of the tubular member 12 prior to use.

With reference now to FIG. 3, a human body 52 is thereshown having one or more entrapped air pockets 54. With the guard 48 removed, the trocar 42 and the tubular member 12 is inserted into the body 52 until the stop member 28 abuts against the skin 55 of the body 52.

In doing so, the pointed end 44 of the trocar 42 pierces the body 52 and, in conjunction with the tapered end 26 of the tubular member 12, permits easy entry of the tubular member 12 into the body 52. The tubular member 12 is inserted into the air pocket 54 as shown in FIG. 3.

With reference now to FIG. 4, the trocar 42 is then removed from the surgical device 10, thus opening the throughbore 14 of the tubular member 12. The air pockets 54, which are slightly pressurized, then exhaust through the ports 16 and into the throughbore 14 of the tubular member 12. From the throughbore 14, the air from the air pockets enters the balloon 38 which expands slightly and opens the slit 40 to release the air from the air pockets 54 into the interior of the bell-shaped housing 32. The entrapped air in turn escapes through the opening 34 in the housing 32.

Once the entrapped air from the air pockets 54 has exhausted through the balloon 38, the balloon slit 40 closes and prevents the entry of contaminants into the human body 52 through the tubular member 14. The surgical device 10 is then removed from the human body 52 which causes a slight suction and removes all residual air remaining in or around the air pocket 54. It should also be noted from FIG. 4 that since each port 16 is formed with sloping sides 17, both insertion and removal of the tubular member 12 is achieved without excessive injury to the body tissues.

From the foregoing, it can be seen that the present invention provides a simple, inexpensive, and yet totally effective means for releasing entrapped air pockets within the human body. Moreover, it should also be apparent that the device 10 of the present invention can be made in varying sizes and lengths to accommodate air pockets 54 at varying depths in adults and children.

Having described my invention, many modifications thereto will become apparent to those skilled in the art to which it pertains without deviation from the spirit of the invention as defined by the scope of the appended claims.

I claim:
1. A pleural decompression catheter comprising, an elongated member adapted to be inserted into a human body so that one end of the elongated member extends outwardly from the body, said elongated member having fluid passage means formed therein for establishing fluid communication between at least one point on the exterior of said member and said end of said member whereby upon insertion of said member in the body, entrapped air within the human body can be exhausted through said fluid passage means and exteriorly of the body;
one-way valve means coupled to said end of said member for permitting fluid flow from said passage means and through said valve means; wherein said passage means comprises an axial throughbore in said elongated member, and said catheter further comprises a trocar removably inserted through said throughbore and said valve means so that said trocar extends outwardly from the other end of said elongated member to thereby aid in inserting said member into said body, said trocar having a diameter substantially equal to the diameter of said throughbore so that the entire periphery of the inserted portion of the trocar abuts against the wall defining said axial throughbore.

2. The invention as defined in claim 1 wherein said passage means further comprises at least one radial port open to said axial bore in said elongated member.

3. The invention as defined in claim 1 and including stop means secured to said elongated member for limiting the insertion of said elongated member into the body.

4. The invention as defined in claim 1 wherein said valve means is a flutter-type valve.

5. The invention as defined in claim 1 wherein said valve means comprises a resilient balloon secured onto and enclosing said end of said member, said balloon having a slit formed therethrough.

6. The invention as defined in claim 1 wherein the other end of said elongated member is tapered inwardly.

7. The invention as defined in claim 1 and further comprising a housing secured to said end of said elongated member, said valve means being contained within the interior of said housing, said housing having at least one opening for exhausting air.

* * * * *